US007221733B1

(12) United States Patent
Takai et al.

(10) Patent No.: US 7,221,733 B1
(45) Date of Patent: May 22, 2007

(54) METHOD AND APPARATUS FOR IRRADIATING A TARGET

(75) Inventors: Yoshihiro Takai, Sendai (JP); Wolfgang Walter Kaissl, Wil/Zunich (CH); Marcel R. Marc, San Jose, CA (US); John C. Ford, Madison, TN (US); Shogo Yamada, Sendai (JP); Masatoshi Mitsuya, Sendai (JP)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 136 days.

(21) Appl. No.: 10/037,477

(22) Filed: Jan. 2, 2002

(51) Int. Cl.
*A61N 5/10* (2006.01)
*A61N 5/01* (2006.01)

(52) U.S. Cl. .............................. 378/65; 378/69; 378/95

(58) Field of Classification Search .................. 378/65, 378/69, 95
See application file for complete search history.

(56) References Cited

U.S. PATENT DOCUMENTS

| | | | | |
|---|---|---|---|---|
| 5,008,907 A | * | 4/1991 | Norman et al. ................ 378/65 |
| 5,207,223 A | | 5/1993 | Adler ....................... 128/653.1 |
| 5,427,097 A | * | 6/1995 | Depp ........................... 600/427 |
| 5,727,554 A | | 3/1998 | Kalend et al. ............ 128/653.1 |
| 5,823,192 A | | 10/1998 | Kalend et al. ............... 128/845 |
| 6,020,159 A | | 2/2000 | Black et al. ................ 435/69.1 |
| 6,138,302 A | | 10/2000 | Sashin et al. ................... 5/600 |
| 6,144,875 A | | 11/2000 | Schweikard et al. ......... 600/427 |
| 6,222,901 B1 | | 4/2001 | Meulenbrugge et al. ....... 378/19 |
| 6,266,393 B1 | * | 7/2001 | Ein-Gal ....................... 378/152 |
| 6,307,914 B1 | * | 10/2001 | Kunieda et al. ............... 378/65 |
| 6,385,288 B1 | * | 5/2002 | Kanematsu ................... 378/65 |
| 6,459,769 B1 | * | 10/2002 | Cosman ...................... 378/147 |
| 6,480,560 B2 | * | 11/2002 | Hsieh ............................ 378/8 |
| 6,526,123 B2 | * | 2/2003 | Ein-Gal ....................... 378/152 |
| 6,600,810 B1 | * | 7/2003 | Hughes ....................... 378/152 |
| 6,621,889 B1 | * | 9/2003 | Mostafavi ..................... 378/65 |
| 6,721,386 B2 | * | 4/2004 | Bulkes et al. ................... 378/8 |
| 6,778,850 B1 | * | 8/2004 | Adler et al. ................. 600/427 |
| 6,865,248 B1 | * | 3/2005 | Rasche et al. .................. 378/8 |
| 6,937,696 B1 | * | 8/2005 | Mostafavi ..................... 378/95 |
| 2003/0007601 A1 | | 1/2003 | Jaffray et al. | |

OTHER PUBLICATIONS

B.J. Lopresti, et al., "Implementation and Performance of an Optical Motion Tracking System for High Resolution Brain PET Imaging", *IEEE Transactions on Nuclear Science*, vol. 46, No. 6, Dec. 1999; pp. 2059-2067.

(Continued)

*Primary Examiner*—Edward J. Glick
*Assistant Examiner*—Thomas R. Artman
(74) *Attorney, Agent, or Firm*—Bingham McCutchen LLP

(57) ABSTRACT

An apparatus (10) for irradiating a target includes a radiation source (12) for generating a radiation beam and a multiple leaf beam adjuster (16) for collimating and adjusting the shape of the radiation beam from the radiation source (12) that would be projected on the target. An image detector (17) detects generates an image signal of the target. In response to the image signal, a control module (18) generate a beam adjustment signal for controlling the beam adjuster (16), thereby enabling the radiation beam from the radiation source (12) to track the movement of the target.

37 Claims, 3 Drawing Sheets

OTHER PUBLICATIONS

P.J Keall, et al., "Motion adaptive x-ray therapy: a feasibility study", *Physics in Medicine Biology*, 46 (2001) 1-10.

Paul Keall, "4D IMRT: Imaging, Planning and Delivery", Jan. 31, 2001, pp. 1-53.

Yonesaka A. et al., "Application of real-time tracking radiation therapy (RTRT) system for the treatment of spinal and paraspinal diseases"; *J. Radiat Oncol. Biol. Phys.*, 2001; 51 (3S1): Abstract No. 44., PMID: 14; 2 pp.

Jolesz, Ferenc, A., M.D., "Image-Guided Procedures and the Operating Room of the Future"; *Brigham and Women's Hospital, Harvard Medical School*; pp. 1-23.

Shimizu, S., et al., Fluoroscopic Real-Time Tumor-Tracking Radiation Treatment (RTRT) Can Reduce Internal Margin (IM) and Set-up Margin (SM) of Planning Target Volume (PTV for Lung Tumors; 2 pp.

Kitamura, K., et al., "Migration of the Internal Fiducial Gold Marker Implanted into Prostate and Liver treated with Real-Time Tumor-Tracking Radiation Treatment (RTRT)", *Hokkaido University School of Medicine*, Sapporo, Japan; 2 pp.

Kitamura, Kei et al.; "3D Intra-Fractional Movement of Prostate Measured During Real-Time Tumor Tracking Radiation Therapy [RTRT] in Supine and Prone Treatment Positions"; *Department of Radiology and Urology, Hokkaido University School of Medicine*; 15 pp.

Fujita K., "Three-dimensional conformal set-up of prostate cancer by adjustment of actual clinical target volume (CTV) to virtual CTV using three fiducial markers and fluoroscopic real-time tracking system.", *J. Radiat. Oncol. Biol. Phys.*, 2001; 51(3S1): Abstract No. 2303, PMID: 16; 2 pp.

Benedit, Stanley H., "Looking Into Patient Positioning and Organ Motion", *VCU Health Sytsem*, pp. 1-10.

Balter, J. M. et al., "Daily targeting of intrahepatic tumors for radiotherapy," *Int J Radiat Oncol Biol Phys*, Jan. 1, 2002:52(1), pp. 266-271.

Cho, P.S. et al. "Cone-beam CT for radiotherapy applications," *Phys Med Biol* 1995;40: pp. 1863-1883.

Drake, D.G. et al. "Characterization of a fluoroscopic imaging system for kilovoltage and megavoltage radiography," *Med Phys* 2000;27: pp. 898-905.

Fahrig, R. et al., "Three-dimensional computed tomographic reconstruction using a C-arm mounted XRII: Imagebased correction of gantry motion non-idealities," *Med Phys* 2000,27:30-38.

Feldkamp, L.A. et al. "Practical cone-beam algorithm," *J Opt Soc Am A* 1984;1: pp. 612-619.

Groh, B.A. et al. "A performance comparison of flat-panel imager-based MV and kV conebeam CT," *Med Phys* 2002;29: pp. 967-975.

Jaffray, D.A. et al. "A radiographic and tomographic imaging system integrated into a medical linear accelerator for localization of bone and soft-tissue targets," *Int J Radiat Oncol Biol Phys* 1999;45: pp. 773-789.

Jaffray, D.A. et al. "Cone-beam computed tomography with a flat-panel imager: Initial performance characterization," *Med Phys* 2000;27: pp. 1311-1323.

Keall, P. J. et al., "[Abstract] Motion Adaptive X-ray Therapy: A feasibility study," 3rd *Annual IMRT Symposium ABSTRACTS*, Chicago 2000 World Congress, Jul. 24, 2000, Sheraton Chicago, Chicago, Illinois.

Keall, P. J. et al., "[Presentation] Motion Adaptive X-Ray Therapy; A Feasibility Study," Medical College of Virginia Hospitals, Virginia Commonwealth University.

Midgley, S., et al. "A feasibility study for megavoltage cone beam CT using commercial EPID," *Phys Med Biol* 1998;43: pp. 155-169.

Mosleh-Shirazi, M.A. et al. "A cone-beam megavoltage CT scanner for treatment verification in conformal radiotherapy," *Radiother Oncol* 1998; 48: pp. 319-328.

Nakagawa, K, et al. "Megavoltage CT-assisted stereotactic radiosurgery for thoracic tumors: Original research in the treatment of thoracic neoplasms," *Int J Radiat Oncol Biol Phys* 2000; pp. 48:449-457.

Pisani, L. et al. "Setup error in radiotherap: On-line correction using electronic kilovoltage and megavoltage radiographs," *Int J Radiat Oncol Biol Phys* 2000; 47: pp. 825-839.

Ruchala, K.J. et al. "Megavoltage CT on tomotherapy system," *Phys Med Biol* 1999; 44: pp. 2597-2621.

Siewerdsen, J.H. et al., "Cone-beam computed tomography with a flat-panel imager: Magnitude and effects of x-ray scatter," *Med Phys* 2001;28: pp. 220-231.

Siewerdsen, J.H., et al., "Optimization of x-ray imaging geometry (with specific application to flat-panel cone-beam computed tomography)," *Med Phys* 2000;27: pp. 1903-1914.

Swindell, W. et al., "Computed tomography with a linear accelerator with radiotherapy application," *Med Phys*, 10, pp. 416-420.

Uematsu, M. et al. "A dual computed tomography linear accelerator unit for stereotactic radiation therapy: A new approach without cranially fixated stereotactic frames," *Int J Radiat Oncol Biol Phys* 1996;35: pp. 587-592.

Uematsu, M. et al. "Intrafractional tumor position stability during computed tomography (CT)-guided frameless stereotactic radiation therapy for lung or liver cancers with a fusion of CT and linear accelerator (FOCAL) unit," *Int J Radiat Oncol Biol Phys* 2000;48: pp. 443-448.

Uematsu, Minoru, et al. "Daily Positioning Accuracy of Frameless Stereotactic Radiation Therapy with a Fusion of computed Tomography and Linear Accelerator (Focal) Unit: Evaluation of z-axis with a z-marker"; *Radiotherapy and Oncology*; vol. 50, Issue 3, Mar. 1, 1999, pp. 337-339.

\* cited by examiner

METHOD AND APPARATUS FOR IRRADIATING A TARGET

FIELD OF THE INVENTION

The present invention relates, in general, to irradiating a target and, more particularly, to adjusting a radiation beam to track the motion of the target.

BACKGROUND OF THE INVENTION

Radiation therapy is widely used for the treatment of tumors. A course of radiation therapy typically includes a planning session and one or more treatment sessions. During the planning session, an oncologist obtains information describing the nature, location, size, and shape of the tumor. Based on the information, the oncologist develops a treatment plan that includes such parameters as radiation beam energy, radiation dose, treatment duration, etc. The treatment plan is executed during the treatment sessions.

In an intensity modulated radiation therapy (IMRT), the radiation intensity projected onto different parts of the tumor can be adjusted according to the treatment plan. The intensity modulation enables the oncologist to adjust the radiation dose received by different parts of the patient's body. Using IMRT, the oncologist can deliver a high radiation dose to the tumor, thereby increasing the therapy efficiency and reducing the inadvertent radiation exposure of the healthy tissues surrounding the tumor.

During a treatment session, the tumor may move due to the breathing or gastric and intestinal movements of the patient. Breathing motion momentarily and repeatedly causes the tumor to move out of the radiation beam and subjects the healthy tissues surrounding the tumor to the radiation. Training the patient for proper breathing techniques may reduce, but not eliminate, the movement of some tumors. The physiological gating of the radiation beam during the treatment session may also reduce the radiation exposure of the healthy tissues by switching off the radiation beam when the tumor moves out of the projected area of the radiation beam. In one gating process, the movement of the tumor is approximated as sinusoidal with a frequency equal to the inhale/exhale frequency of the patient. In another gating process, markers are placed on patient's thorax and/or abdomen to facilitate the detection of patient breathing and/or gastric and intestinal movements. Although the physiological gating process can reduce the radiation exposure of the tissues surrounding the tumor, it may prolong the duration of the treatment session by periodically switching off the radiation beam. This may reduce the throughput of the radiation therapy.

According, it would be advantageous to have an apparatus and a method for tracking the tumor movement during a radiation treatment therapy. It would also be advantageous for the apparatus and the method to be able to adjust the radiation beam in response to the tumor movement. It would be of further advantage if the apparatus can be made by modifying an existing radiation therapy apparatus.

SUMMARY OF THE INVENTION

In one aspect, the present invention provides an apparatus and a method for irradiating a target. In a specific aspect, the present invention provides an apparatus and a process for detecting a movement of the target and dynamically adjusting a radiation beam to track the target.

In accordance with one embodiment of the present invention, an apparatus for irradiating a target includes a radiation source that generates a radiation beam, e.g., a cone shaped radiation beam, and a beam adjuster, e.g., a multiple leaf collimator, for collimating and adjusting the shape of the radiation beam from the radiation source that would be projected onto the target. An image detector detects the image beam and generates an image signal of the target. The target signal is used to generate a beam adjustment signal for controlling the beam adjuster, thereby enabling the radiation beam generated by the radiation source to track the target.

In accordance with a specific embodiment of the present invention, the apparatus and the method are used for radiation treatment of tumors. Fiducial markers may be coupled to the target, i.e., the tumor under the radiation treatment. The fiducial markers form a sharp image on the image detector when illuminated by an image beam, e.g., a low energy X-ray beam, thereby indicating the location, orientation, shape, and/or size of the tumor to be treated under the radiation therapy.

In accordance with another specific embodiment of the present invention, a radiation treatment apparatus includes a radiation source that generates a radiation beam and a beam adjuster, e.g., a multiple leaf collimator, for collimating and adjusting the shape of the radiation beam from the radiation source that would be projected onto the patient. An image detector, e.g., a video camera, detects the images of an external marker placed on the thorax and/or abdomen of the patient and generates an image signal of the external marker. Using a previously established relationship between the tumor movement and the marker positions, a beam adjustment signal for controlling the beam adjuster is generated in response to the image signal of the external markers, thereby enabling the radiation beam to track the tumor.

In accordance with various alternative embodiments of the present invention, the radiation beam can track the target by moving a gantry on which the radiation source is mounted, by moving a platform on which the target is placed. Tracking through the beam adjuster as described herein above can be used in any combination with these and other processes. In addition, a process of irradiating a target can also incorporate a gating process that temporarily switches off the radiation source in response to a sudden target movement.

DETAILED DESCRIPTION OF THE PREFERRED EMBODIMENTS

Figure 1:
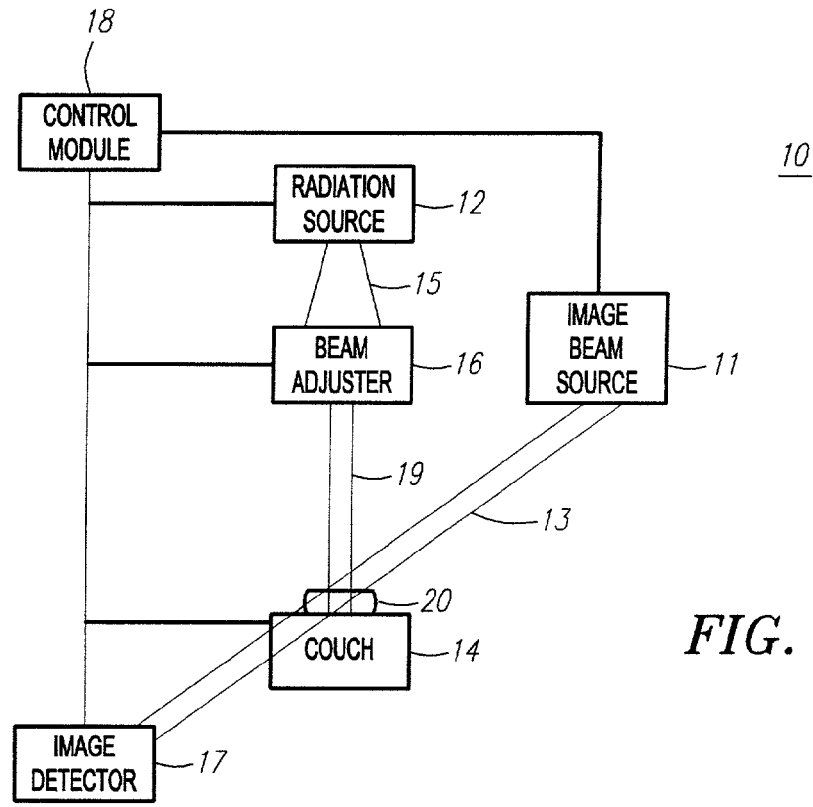
FIG. 1 is a functional block diagram illustrating a radiation apparatus in accordance with the present invention.

Preferred embodiments of the present invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an aspect described in conjunction with a particular embodiment of the present invention is not necessarily limited to that embodiment and can be practiced in any other embodiments of the present invention.

FIG. 1 is a functional block diagram illustrating a radiation therapy apparatus 10 in accordance with the present invention. Apparatus 10 includes a radiation source 12. By way of example, radiation source 12 generates X-ray radiation at a mega-volt (MV) energy spectrum in a radiation beam 15 toward a platform or a couch 14. A beam adjuster 16 is located between radiation source 12 and couch 14 and functions to adjust the shape, size, and direction of a radiation beam 19 reaching a patient 100 on couch 14 during a radiation treatment session. Apparatus 10 also includes a control module 18 coupled to radiation source 12, couch 14, and beam adjuster 16 to control their operations. In addition, apparatus 10 includes an image beam source 11 and an image detector 17 coupled to control module 18. By way of example, image beam source 11 generates a low energy X-ray beam 13 at a kilo-volt (kV) level, and image detector 17 is an X-ray image detector.

In accordance with one embodiment of the present invention, control module 18 includes a signal processor such as, for example, a digital signal processor (DSP), a central processing unit (CPU), or a microprocessor (µP), and a memory coupled to the signal processor. The memory serves to store a treatment plan for patient 100 and other programs for the operation of apparatus 10. The signal processor executes the programs and generates signals for the operation of radiation source 12, couch 14, beam adjuster 16, image beam source 11, and image detector 17. The signal processor also receives image signals from image detector 17 and generates tracking signals in response to thereto.

It should be noted that apparatus 10 in accordance with the present invention is not limited to having the structure as describe herein above. For example, radiation source 12 is not limited to generating X-ray radiation beam 15 at the MV energy spectrum. Depending on the nature of treatment or application, radiation source 12 may generate X-ray radiation at other energy spectrums or generate other kinds of radiation beams, which include, but are not limited to, beta ray beams, positron beams, proton beams, antiproton beams, neutron beams, heavy ion beams, e.g., alpha ray beams, carbon ion beams, etc. Likewise, image beam source 11 is not limited to generating X-ray radiation beam 13 in the kV energy spectrum. Further, apparatus 10 is not limited to having one image beam source 11 and one image detector 17 as shown in FIG. 1. In alternative embodiments, apparatus 10 may include two or more image beam sources and two or more image detectors. For example, a plurality of image beam sources and image detectors are generally required for providing stereotaxic data.

In accordance with an alternative embodiment of the present invention, apparatus 10 does not include image beam source 11. Image detector 17 in apparatus 10 includes one or more video cameras for generating images signals regarding the external anatomy of patient 100. In accordance with another alternative embodiment, image detector 17 includes a magnetic field detector for generating image signals by detecting one or more magnetic markers or seeds implanted in patient 100.

Figure 2:
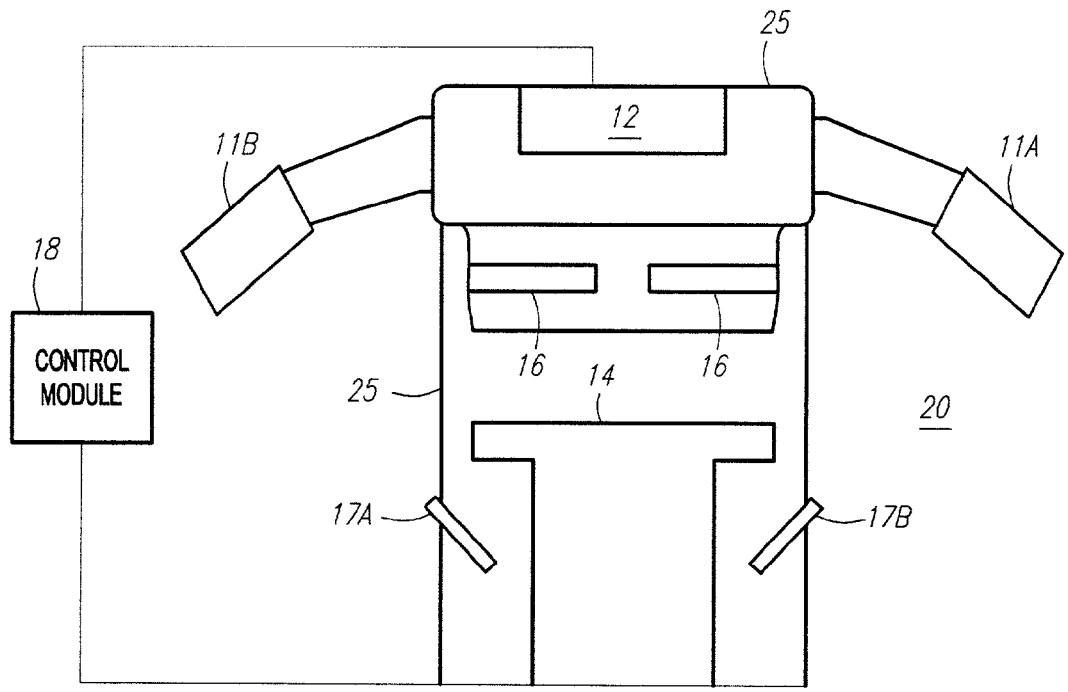
FIG. 2 illustrates a radiation apparatus in accordance with an embodiment of the present invention.

FIG. 2 is a schematic diagram illustrating a radiation therapy apparatus 20 in accordance with an embodiment of the present invention. The functional structure of apparatus 20 is similar to that of apparatus 10 described herein above with reference to FIG. 1. Apparatus 20 includes a gantry 25 positioned over platform or couch 14 and housing radiation source 12 and beam adjuster 16. In a preferred embodiment, gantry 25 is capable of rotating around couch 14 so that the radiation beam generated by radiation source 12 can be projected onto a patient on couch 14 at different angles. Apparatus 20 also includes two image beam sources, 11A and 11B, mechanically coupled to the opposite sides of gantry 25. Two image detectors, 17A and 17B, are also mechanically coupled to gantry 25 (not shown in FIG. 2). Preferably, the positions and orientations of image bean sources 11A and 11B and image detectors 17A and 17B are adjustable to accommodate different patients. A control module 18 controls the operation of apparatus 20.

In operation, control module 18 processes the image signals from image detectors 17A and 17B to calculate the data regarding the position, shape, and/or size of the tumor in the patient. These data are used to generate beam adjustment signals to control beam adjuster 16, thereby adjusting the position of the radiation beam projected on the patient. In alternative embodiments, the beam adjustment signals can also control gantry 25 for changing beam position and/or control couch 14 for repositioning the patient. In general, any combination of the movements of beam adjuster 16, gantry 25, and couch 14 may be used to cause the position of the radiation beam to track the movement of target. Accordingly, discussion of any mode of target tracking herein does not preclude use of other modes in addition to the mode under discussion. The control signal can additionally be used for switching the radiation beam on and off in a gating process, as will be described in more detail below.

Apparatus 20 is not limited to having two image beam source, 11A and 11B, and two image detectors, 17A and 17B, as shown in FIG. 2. Depending on the desired accuracy of the tumor movement tracking, apparatus 20 can have only one image beam source and one image detector, or have more than two image beam sources and more than two image detectors. Furthermore, image beam sources 11A and 11B and image detectors 17A and 17B are not limited to being mechanically coupled to gantry 25. In an alternative embodiment, image beam sources 11A and 11B are mounted on the ceiling of a treatment room, in which apparatus 20 is installed. Likewise, image detectors 17A and 17B can be mounted on couch 14 or in the floor of the treatment room.

In accordance an alternative embodiment of the present invention, the radiation beam generated by radiation source 12 serves as both a radiation treatment beam and an image forming beam. Apparatus 20 includes an image detector (not shown in FIG. 2) for detecting the images of the target or fiducial markers on the patient formed by the radiation beam generated by radiation source 12. In a typical radiation treatment therapy, the radiation beam generated by radiation source 12 is a high energy X-ray beam at an MV energy spectrum. On the other hand, the image beam generated by image beam source 11A or 11B typically has a kV energy spectrum. A system using X-ray radiation at different energy spectrums for imaging is described in U.S. patent application Ser. No. 10/033,327 entitled "RADIOTHERAPY APPARATUS EQUIPPED WITH AN ARTICULABLE GANTRY FOR POSITIONING AN IMAGING UNIT" and filed on Nov. 2, 2001 and U.S. patent application Ser. No. 10/013,199 entitled "X-RAY IMAGE ACQUISITION APPARATUS" and filed on Nov. 2, 2001, which are incorporated herein by reference in their entireties.

Figure 3:
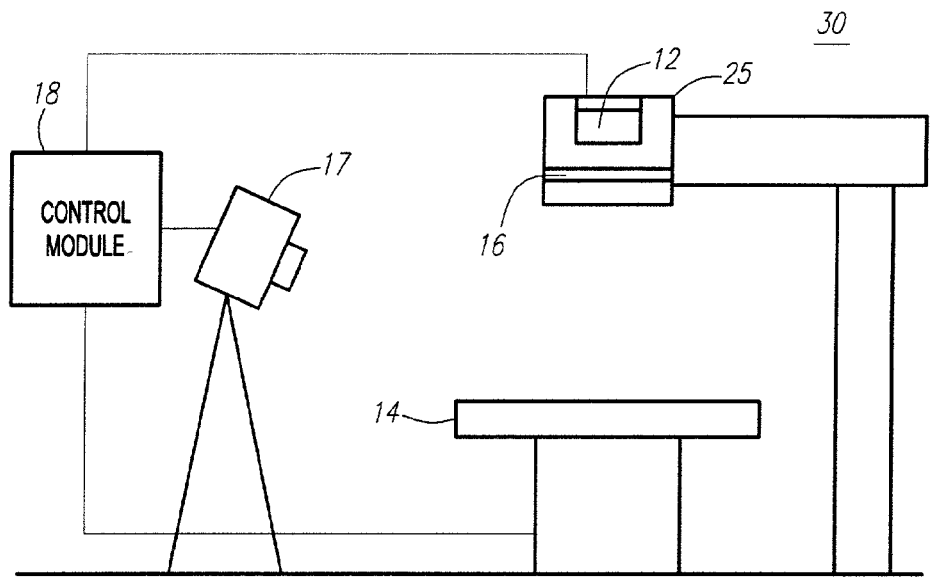
FIG. 3 illustrates a radiation apparatus in accordance with another embodiments of the present invention.

FIG. 3 is a schematic diagram illustrating a radiation therapy apparatus 30 in accordance with another embodiment of the present invention. Like apparatus 20 shown in FIG. 2, apparatus 30 includes gantry 25 positioned over platform or couch 14 and housing radiation source 12 and beam adjuster 16. In a preferred embodiment, gantry 25 is capable of rotating around couch 14 so that the radiation beam generated by radiation source 12 can be projected onto a patient on couch 14 at different angles. Apparatus 30 is used in conjunction with an image detector 17, which is, by way of example, a video camera. Typically, video camera 17 is room mounted. Preferably, the position and orientation of video camera image detector 17 are adjustable to accommodate different patients under treatment.

In operation, video camera image detector 17 generates image signals regarding the external anatomy of the patient, or one or more external markers placed on the patient. Control module 18 processes the image signals from video camera image detector 17 to deduce the data regarding the position, shape, and/or size of the tumor using an established relationship between the tumor position, shape and/or size and the external anatomy of the patient or the marker. These data are used to generate beam adjustment signals to control beam adjuster 16, thereby adjusting the position of the radiation beam projected on the patient. In alternative embodiments of the present invention, the beam adjustment signals can also control radiation source 12 for gating, control gantry 25 for changing beam direction, and/or control couch 14 for repositioning the patient.

Apparatus 30 is not limited to having one video camera image detector 17 as shown in FIG. 3. Depending on the desired accuracy of the tumor movement tracking, apparatus 30 can have more than one image detectors for stereotaxic information of the patient's anatomy. Further, apparatus 30 can also include image beam sources and corresponding image detectors like those shown in FIG. 2, thereby enabling apparatus 30 to generate both external and internal anatomical or marker data of the patient. In addition, apparatus 30 can include magnetic field detectors to detect the magnetic field of magnetic seeds implanted in the patient.

Figure 4:
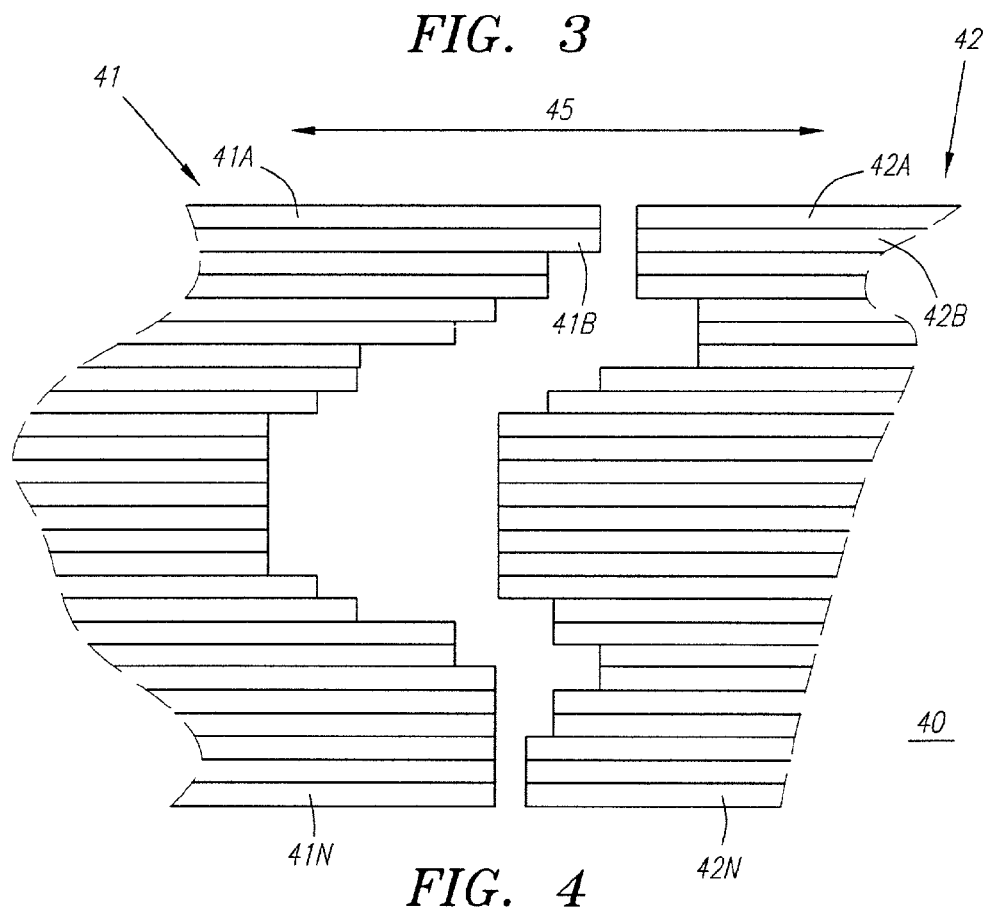
FIG. 4 illustrate a multiple leaf collimator in accordance with an embodiment of the present invention.

FIG. 4 is a schematic diagram illustrating a multiple leaf collimator 40 that can function as beam adjuster 16 shown in FIGS. 1, 2, and 3 in accordance with an embodiment of the present invention. Multiple leaf collimator (MLC) 40 includes a first row 41 of multiple leaves 41A, 41B, . . . , and 41N, and a second row 42 of multiple leaves 42A, 42B, . . . , and 42N. Multiple leaves 41A–41N in row 41 are parallel to each other. Likewise, multiple leaves 42A–42N in row 42 are parallel to each other. Further, row 41 of leaves 41A–41N and row 42 of leaves 42A–42N are opposite to each other. Each of multiple leaves 41A–41N in row 41 and each of multiple leaves 42A–42N in row 42 is individually movable in a direction indicated by a double ended arrow 45 in FIG. 4. Leaves 41A–41N and 42A–42N in MLC 40 are preferably made of such a material that enable them to effectively block the radiation generated by radiation source 12. Materials typically suitable for leaves 41A–41N and 42A–42N in MLC 40 include tungsten, tantalum, lead, etc.

In operation, a control module, e.g., control module 18 shown in diagram FIGS. 1, 2, and 3, controls the motion of mulitple leaves 41A–41N and 42A–42N to shape the radiation beam generated by radiation source 12. The radiation beam shaped by MCL 40 preferably irradiates the tumor in a patient on couch 14 with minimum radiation exposure on the healthy tissues surrounding the tumor. In one embodiment, control module 18 adjusts MLC 40 to shape the radiation beam to be conformal to the tumor in the patient. In another embodiment, control module 18 adjusts MLC 40 to both shape the radiation beam to be conformal to the tumor and modulate the intensity of the radiation beam projected on the patient.

The number of leaves 41A–41N and 42A–42N in MLC 40 can have a wide range. Generally, an MLC having a large number of narrow leaves has a higher resolution than an MLC having a small number of thick leaves. A high resolution is generally beneficial in shaping the radiation beam precisely to the shape of the tumor and modulating the radiation intensity precisely. In one example, each of rows 41 and 42 in MLC 40 includes forty leaves. In another example, each of rows 41 and 42 in MLC 40 includes 75 leaves.

Multiple movable leaves 41A–41N and 42A–42N in MLC 40 are not limited to being straight and parallel to each other as shown in FIG. 4. They can be curved or bent. Certain shapes and arrangements for leaves 41A–41N and 42A–42N may benefit the manufacturing, operation, and/or maintenance of MLC 40. These and other design variations for MCL 40 are within the scope of the present invention.

In an alternative embodiment of the present invention, beam adjuster 16 includes two multiple leaf collimator, each like MLC 40 shown in FIG. 4, with one collimator stacked over the other collimator. The multiple leaves in one MLC are at an angle, e.g., 90 degrees (°), with respect to the multiple leaves in the other MLC. Such an arrangement of two MLCs stacked over each other is also referred to as a biplanar multiple leaf collimator. Beam adjuster 16 including two MLCs arranged as a biplanar MLC is capable of shaping the radiation beam in more diverse shapes than that including only one MLC. It should be noted that the angle between the leaves of the two MLCs in a biplanar MLC is not limited to being 90°. In accordance with the present invention, the leaves in the two MLCs are preferably not parallel to each other, thereby rendering beam adjuster 16 higher degrees of freedom in adjusting shape of the radiation beam than a beam adjuster with only one MLC.

Figure 5:
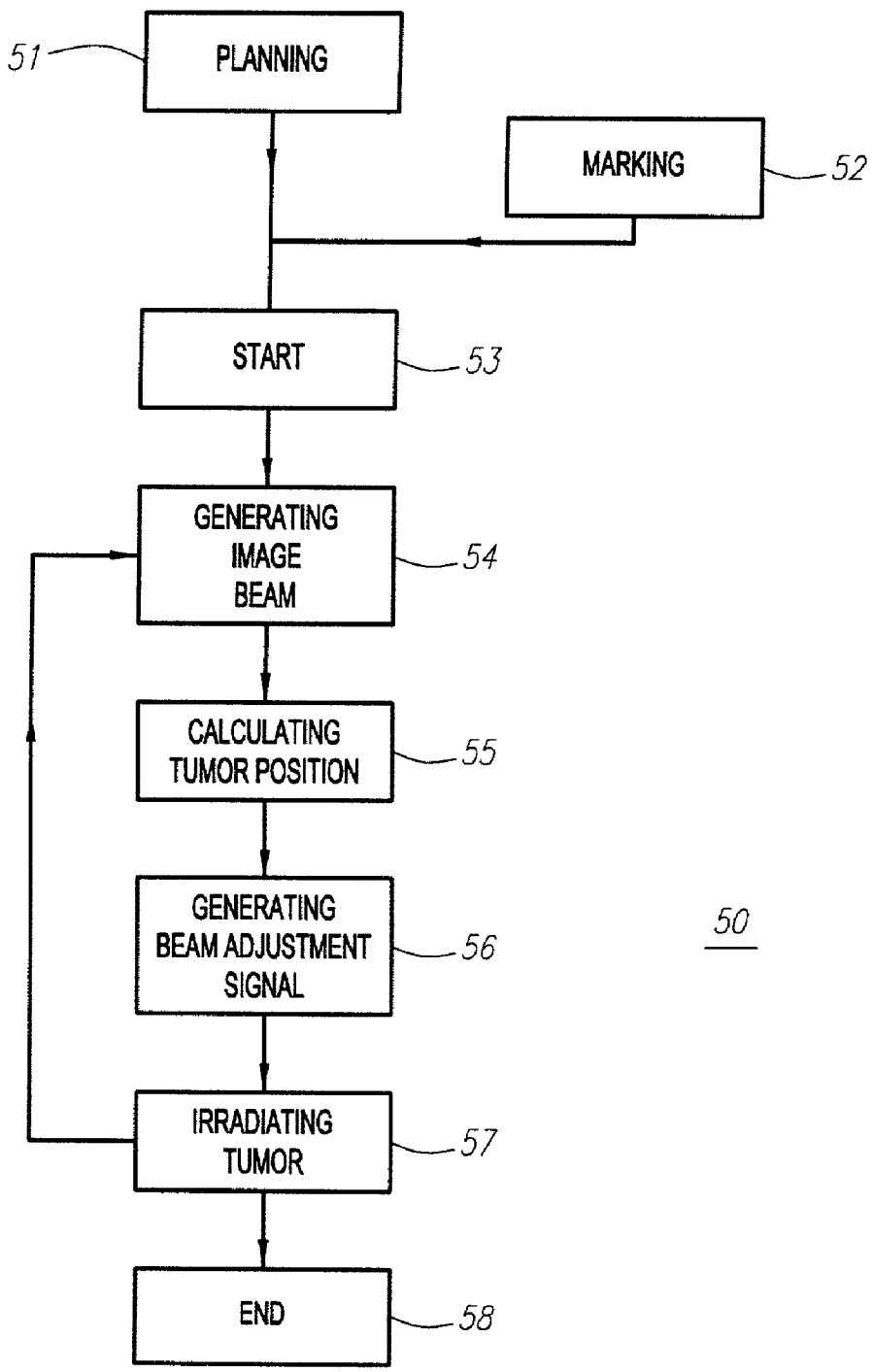
FIG. 5 is a flowchart illustrating a radiation therapy process in accordance with the present invention.

FIG. 5 is a flowchart schematically illustrating a radiation therapy process 50 in accordance with a specific embodiment of the present invention. By way of example, radiation treatment process 50 can be performed using apparatus 10, 20, and 30 described herein above with reference to FIGS. 1, 2, and 3, respectively.

In a planning step 51, a treatment plan for a patient is established based on the nature, size, shape, and location of the tumor in the patient. In accordance with one embodiment of the present invention, the treatment plan preferably includes data regarding the radiation doses different portions of the tumor should receive. Typically, the treatment plan will set forth several treatment sessions, which are also referred to as fractions. During each fraction, the patient may receive radiation from several angles. Each such angle for receiving radiation is referred to as a field. For each field, the treatment plan calculates the shape of the beam and the time duration the radiation beam should be applied. By applying radiation at several fields, with the shape of the beam optimized to account for the cross sectional shape of the tumor and other anatomical factors, a conformal dose is delivered. In general, the tracking of tumor movement described herein is the motion that occurs while executing the plan for a single field.

In an intensity modulated radiation therapy (IMRT), while each field is being executed, the multiple leaves in MLC beam adjuster 16 move so that different portions of the tumor cross-section receive different amounts of radiation. For example, if one part of the tumor is close to a critical or sensitive structure, the leaves in MLC beam adjuster 16 may block the radiation near that part during some portion of the field, thereby decreasing the radiation dose receiving by that part of the tumor and minimizing the possible adverse effect of the radiation exposure by the critical or sensitive structure. When moving of the multiple leaves in MLC beam adjuster 16 to track the tumor movement in conjunction with an IMRT plan, the motion of the leaves to achieve IMRT will be superimposed on the motion of the leaves to track the tumor. In a standard IMRT treatment process, the IMRT motion is calculated for each field. In accordance with an embodiment of the present invention, it is generally sufficient to use the IMRT plan for a field calculated at some phase within a breathing cycle. Alternatively, a separate IMRT plan can be calculated for each of a plurality of phases in a breathing cycle in each field.

In accordance with another embodiment, the relationship between the tumor movement and the patient's breathing is established during treatment planning step 51. Such relationship can be obtained by imaging the tumor at various phases of the patient's breathing cycle. Techniques suitable for imaging the tumor at planning step 51 include planar radiography, ultrasound (US), computed tomography (CT), single photon emission computed tomography (SPECT), magnetic resonance imaging (MRI), magnetic resonance spectroscopy (MRS), positron emission tomography (PET), etc. The established relationship between the tumor movement and the patient's breathing facilitates the prediction of the tumor movement. In accordance with yet another embodiment, the relationship between the tumor movement and patient's thorax and abdomen movement is established. The established treatment plan is stored in control module 18.

In a marking step 52, one or more fiducial markers having a known position relative to the tumor are provided. In accordance with one embodiment, the markers are implanted into the patient. Depending on the nature and location of the tumor, the fiducial markers may be implanted on the tumor or in the tissues surrounding the tumor. In another embodiment, fiducial markers are placed on the thorax and/or abdomen of the patient.

A fiducial marker can have various shapes, e.g., spherical, elongated cylindrical, etc. In accordance with one embodiment, a fiducial marker is a metal cylinder having a diameter ranging between approximately 0.5 millimeter (mm) and approximately 1 mm and a length ranging between approximately 2 mm and approximately 4 mm. In accordance another embodiment of the present invention, a fiducial marker has an asymmetric three-dimensional structure that enables the determination of its location and orientation through a single image. Fiducial markers having asymmetric structures are described in U.S. patent application Ser. No. 09/178,383 entitled "METHOD AND SYSTEM FOR PREDICTIVE PHYSIOLOGICAL GATING OR RADIATION THERAPY" and filed on Oct. 23, 1998, U.S. patent application Ser. No. 09/712,724 entitled "METHOD AND SYSTEM FOR PREDICTIVE PHYSIOLOGICAL GATING OF RADIATION THERAPY" and filed on Nov. 24, 2000, and U.S. patent application Ser. No. 09/893,122 entitled "METHOD AND SYSTEM FOR PREDICTIVE PHYSIOLOGICAL GATING" and filed on Jun. 26, 2001, which are incorporated herein by reference in their entireties.

The composition of the fiducial markers preferably has a stable chemical property that does not have significant reaction with the tissues surrounding the marker. The stable chemical property is especially preferred for internal markers to be implanted into the patient. Further, the composition of the fiducial markers is preferably substantially opaque to the image beam generated by image bean source 11, thereby forming a sharp image on image detector 17. Appropriate materials for the fiducial markers include, but are not limited to, gold, tungsten, tantalum, titanium, etc. The fiducial markers can also include a radioactive isotope material to enhance the image quality. The fiducial marker can also include paramagnetic or ferromagnetic materials to form magnetic markers or seeds.

After placing the patient on couch 14, the radiation treatment session starts in a start step 53 by activating control module 18 to execute the treatment plan. According the treatment plan, control module 18 generates signals to control the operations of image beam source 11, image detector 17, radiation source 12, beam adjuster 16, couch 14, and gantry 25.

In a step 54, image beam source 11 generates an image forming beam, e.g., a low energy X-ray radiation beam at the kV energy spectrum. The image forming beam illuminates at least a portion of the patient on couch 14 that includes the tumor under treatment and the surrounding area. The image forming beam penetrates the body of the patient and illuminates image detector 17 placed on the opposite side of the patient from image bean source 11. The fiducial markers in the body of the patient partially block the image forming beam, forming images on image detector 17.

In a step 55, image detector 17 generates an image signal of the fiducial markers and transmits the signal to control module 18. Control module 18 processes the image signal and calculates the location, shape, and/or size of the tumor in the patient.

In an alternative embodiment, instead of being implanted into the patient, external markers are placed on the thorax and abdomen of the patient. In this embodiment, radiation therapy process 50 does not include step 54 of generating image forming beam. Further, image detector 17 includes a video camera, as described herein above with reference to FIG. 3, to generate image signals regarding the external markers on the patient. The movement of the tumor is deduced from the images of the external markers through the relationship there between established during treatment planning step 51. Process of deducing tumor positions form the images of external markers is described in U.S. patent application Ser. Nos. 09/178,383, 09/712,724, and 09/893,122, which have been incorporated in their entireties. Generally speaking, the methods and apparatuses for detecting target movement for the purpose of gating the radiation beam can also be used for tracking the tumor movement as described herein. Furthermore, the information about the target movement collected by such methods and apparatuses may be used for tracking the tumor movement, as well as for gating the radiation beam in conjunction with tracking to shut off the radiation beam under certain circumstances.

In another alternative embodiment, radiation therapy process 50 does not include marking step 52 or generating image forming beam step 54. In this embodiment, image detector 17 includes one or more video cameras to generate the image signals regarding external anatomical contour of the patient. The movement of the tumor is deduced from the images of the external anatomical contour through the relationship there between established during treatment planning step 51. In this embodiment, the external anatomical contour of the patient functions as markers to indicate the tumor movement inside the body of the patient.

In yet another alternative embodiment, magnetic seeds are implanted into the patient to serve as fiducial markers. Radiation therapy process 50 does not generating image forming beam step 54. Image detector 17 includes one or more magnetic field detectors or sensors to generate the image signals regarding the positions of the magnetic markers. The movement of the tumor is deduced from the images of the magnetic markers through the relationship there between established during treatment planning step 51.

In a step 56, control module 18 generates a beam adjustment signal in response to the calculated location, shape, and/or size of the tumor as well as the treatment plan. The beam adjustment signal is transmitted to beam adjuster 16 to adjust the position of a radiation beam that will be projected onto the patient from radiation source 12. In accordance with one embodiment of the present invention, control module 18 can also generate a control signal to move couch 14 to reposition the patient, thereby facilitating the focus of the radiation beam onto the tumor in the patient. Repositioning the patient in a radiation therapy is described in U.S. Pat. No. 6,279,579 entitled "METHOD AND SYSTEM FOR POSITIONING PATIENTS FOR MEDICAL TREATMENT PROCEDURES" filed on Oct. 23, 1998 and issued on Aug. 28, 2001, which is incorporated herein by reference in its entirety. In accordance with another embodiment of the present invention, control module 18 can further generate a control signal to move gantry 25, thereby changing the position of the radiation beam projected on the patient.

In a step 57, radiation source 12 is turned on to generate a radiation beam toward couch 14. The radiation beam is collimated and shaped by beam adjuster 16, resulting in a radiation beam irradiating a particular portion, i.e., tumor, of the patient on couch 14.

After radiation source 12 is turned on to irradiate the tumor in the patient, steps 54, 55, 56, and 57 repeat to continuously and dynamically adjust the direction, shape, size, and intensity of the radiation beam projected onto the patient according to the treatment plan and the calculated tumor location, shape, and/or size. Radiation source 12 remains active to continuously to generate the radiation beam, which is collimated and dynamically adjusted by beam adjuster 16 to from the radiation beam projected on the patient. The generation and adjustment of the radiation beam in response to the tumor movement continue until the treatment session ends in a step 58 when the total dose for the treatment session is reached.

A course of treatment for a patient generally includes a plurality of treatment sessions, each session generally having several fields. During each field, control module 18 tracks the movement of the tumor using the image signals generated by image detector 17 and dynamically adjusts the radiation beam projected on the patient through beam adjuster 16.

Radiation treatment process 50 in accordance with the present invention is not limited to being that described herein above. In an alternative embodiment, the relationship between tumor position and the internal anatomy of the patient is established in planning step 51 by such means as planar radiography, US, CT, SPECT, MRI, MRS, PET, etc. In step 55 of radiation treatment process 50, the internal anatomy, e.g., diaphragm movement, lung movement, gastric movement, intestinal movement, of the patient is tracked using image detector 17. Some of the internal anatomical movements, e.g., diaphragm movement, can be tracked without using fiducial markers. Control module 18 deduces the tumor position from the internal anatomy data and generates signal to adjust the radiation beam projected on the patient.

In accordance with one embodiment of the present invention, radiation treatment process 50 incorporates a physiology gating process as that described in U.S. patent application Ser. Nos. 09/178,383, 09/712,724, and 09/893,122, which have been incorporated in their entireties. Specifically, control module 18 may generate a signal to momentarily shut down radiation source 12 in response to the tumor moving in an abnormal pattern. When the tumor resumes its normal movement, e.g., the periodic movement associated with the breathing of the patient, permitting the projection of the radiation beam thereon with minimum exposure to the surrounding tissues, control module 18 turns radiation source 12 back on. For example, sudden and involuntary moves of the patient, e.g., coughing, sneezing, muscle cramping, etc., during a field may move the tumor unpredictably, thereby triggering control module 18 to momentarily shut down radiation source 12. In accordance with various embodiments of the present invention, the gating process can be combined with adjusting the radiation beam through beam adjuster 16, repositioning the patient through moving couch 14, and/or adjusting radiation beam direction through moving gantry 25.

Gating can be used in conjunction with radiation beam tracking in other ways as well. In a typical gating process during normal breathing, the radiation beam is turned on while the tumor is in a portion of the cycle where there is little motion, and turned off for the rest of the cycle. In conjunction with tracking, the radiation beam can be gated off for a lesser portion of the breathing cycle. In accordance with one embodiment of the present invention, if one portion of the cycle has extremely complex tumor motion, rapid motion, or motion for which it is difficult to establish an accurate correlation with marker or anatomical motion, the radiation beam is gated off for the portion, but left on while tracking the motion during the rest of the cycle.

In accordance with one embodiment of the present invention, control module 18 uses the tracking signals to directly control beam adjuster 16 to shape the radiation beam. In other words, the tracking signals are superimposed on the treatment plan in the control of beam adjuster 16. In accordance with another embodiment, the treatment plan is converted to a lookup table that preferably has taken variations in tumor location, shape, and/or size into consideration. The lookup table is stored in the memory of control module 18. In response to the image signals, control module 18 generates the tracking signals. Control module 18 then uses the tracking signals to parse the lookup table to select the appropriate entries in the lookup table to control beam adjuster 16.

The movement of the tumor may include translational motion and rotational motion. The shape of the tumor may also change. To accurately track all these movement and adjust the radiation beam to track the tumor movement may require control module 18 to have a high power signal processor and beam adjuster 16 to have a high resolution and a high degree of freedom in the adjusting the shape of the radiation beam. These requirements can increase the complexity and cost of apparatus 10, 20, or 30. Certain approximations may be made to strike a balance between accurately tracking the tumor movement and reducing the cost of manufacturing, operating, and maintaining apparatus 10, 20, or 30.

In one exemplified embodiment, the tumor is assumed to be substantially rigid and have no significant rotational motion. In this assumption, tracking the tumor requires only three translational coordinates. Because the shape and orientation of the tumor do not change, a single fiducial marker implanted on or near the tumor is sufficient to indicate the location of the tumor. Two image beams not parallel to each other and two corresponding image detectors can accurately track the position of the tumor.

If the movement of the tumor is substantially planar, there are only two degrees of freedom in the movement of the tumor. In this situation, a single image beam is sufficient to track the movement of the tumor. The tracking accuracy may be improved by adjusting the image beam to be substantially perpendicular to the plane in which the tumor moves.

In another exemplified embodiment, the tumor is assumed to be substantially rigid, but can have both translational and rotational movements. In this assumption, tracking the tumor requires three translational coordinates and three rotational coordinates. Multiple fiducial markers may be implanted on or near the tumor to indicate both the location and orientation of the tumor. Alternatively, a signal marker with an asymmetric feature may provide sufficient information in certain cases. Two image beams not parallel to each other and two corresponding images detectors can accurately track the position and orientation of the tumor.

If the rotational motion of the tumor is substantially around an axis having a fixed orientation in space, two markers implanted on or near the tumor not aligned with the rotational axis of the tumor can provide sufficient information regarding the rotational motion of the tumor. In general, four markers implanted on or near the tumor and not coplanar with each other are sufficient in tracking both the translational and rotational motion of the tumor.

If the shape and size of the tumor also change, more markers may be needed. In certain situation where the markers are positioned closely to one another, the markers may be distinctive from each other so that they can easily be individually identified by control module 18. Further, more than two image beams may be required to accurately track the location, shape, and size of the tumor. Fiducial markers having asymmetric three-dimensional structures may be beneficial in tracking the tumor movement with a high degree of freedom.

By now it should be appreciated that an apparatus and a method for irradiating a target have been provided. A radiation process in accordance with the present invention includes tracking the movement of the target and dynamically adjusting the radiation beam in response thereto. This will minimize the radiation exposure of the area surrounding the target. In accordance with one aspect of the present invention, the target to be irradiated is a tumor in a patient. Using the apparatus and the method of the present invention in a radiation therapy can minimize the radiation exposure of the healthy tissues surrounding the tumor under the radiation therapy. The radiation therapy performed in accordance with the present invention is advantageous over the physiology gating process in the sense that the radiation beam does not need to be switched off when the tumor moves during a field, or can be switched off for lesser portion of a breathing cycle. Thus, the radiation treatment process of the present invention is more efficient than that of physiology gating. The apparatus in accordance with the present invention can be easily obtained by upgrading a control module in an existing radiation treatment apparatus. Additional modifications may include mechanically coupling one or more image beam sources and/or one or more image detectors to the existing radiation treatment apparatus.

While specific embodiments of the present invention have been described herein above, they are not intended as a limitation on the scope of the present invention. The present invention encompasses those modifications and variations of the described embodiments that are obvious to those skilled in the art. For example, the method of irradiating a target in accordance with the present invention is not limited to irradiating a tumor in a human patient. The method is equally applicable in veterinarian medical treatment of animals. In addition, the radiation process in accordance with the present invention may find application in other areas such as, for example, agriculture product treatment, biological inspection, mechanical structure inspection, etc.

The invention claimed is:

1. A method for irradiating a target, comprising:
   establishing a relationship of the at least one marker relative to the target by determining a relative position between the at least one marker and the target;
   generating an image signal of the at least one marker;
   generating a tracking signal in response to the image signal; and
   adjusting a radiation beam in response to the tracking signal to track the target;
   wherein the target is tracked while performing an intensity modulated radiotherapy using a first multi-leaf collimator, and wherein in the intensity modulated radiotherapy, a leaf of the first multi-leaf collimator is adjusted such that a first portion of the target receives more radiation than a second portion of the target.

2. The method as claimed in claim 1, wherein:
   the step of generating an image signal includes generating an X-ray image of the at least one marker; and
   the step of generating a tracking signal includes generating the tracking signal to track a movement of the target.

3. The method as claimed in claim 1, wherein the step of generating an image signal includes generating the image signal regarding an anatomy of a patient having a tumor as the target.

4. The method as claimed in claim 1, wherein the step of generating an image signal further includes the steps of:
   illuminating the target and an area near the target with a first beam; and
   detecting a first image of the at least one marker found by the first image beam.

5. The method as claimed in claim 4, wherein the step of generating an image signal further includes the steps of:
   illuminating the target and the area near the target with a second image beam unparallel to the first image bean; and
   detecting a second image of the at least one marker formed by the second image beam.

6. The method as claimed in claim 1, wherein the step of adjusting a radiation beam further includes the steps of:
   superposing the tracking signal on a radiation treatment plan; and
   generating a beam adjustment signal using the treatment plan with the tracking signal superimposed thereon.

7. The method as claimed in claim 1, wherein the first multi-leaf collimator has a plurality of movable leaves arranged in two rows opposite to each other.

8. The method as claimed in claim 7, wherein the step of adjusting a radiation beam further includes adjusting the radiation beam using a second multi-leaf collimator having a plurality of movable leaves arranged in two rows opposite to each other and unparallel to the plurality of leaves of the first multi-leaf collimator.

9. The method as claimed in claim 1, wherein the step of adjusting a radiation beam further includes temporarily switching off the radiation beam in response to the tracking signal having a value indicating the target being outside an area.

10. The method of claim 1, wherein the target is located beyond a head region of a patient.

11. The method of claim 1, wherein the leaf of the first multi-leaf collimator is adjusted for a first field.

12. The method of claim 11, further comprising further adjusting the leaf of the first multi-leaf collimator for a second field.

13. The method of claim 1, wherein the first portion comprises healthy tissue.

14. A method for irradiating a target in an animal body, comprising:
 establishing a relationship of at least one marker relative to the target by determining a relative position between the at least one marker and the target, the at least one marker being placed internally in the animal body;
 generating an image signal of the at least one marker;
 generating a tracking signal in response to the image signal; and
 adjusting a radiation beam in response to the tracking signal to track the target;
 wherein the target is tracked while performing an intensity modulated radiotherapy using a first multi-leaf collimator, and wherein the intensity modulated radiotherapy, a leaf of the first multi-leaf collimator is adjusted such that a first portion of the target receives more radiation than a second portion of the target.

15. The method as claimed in claim 14, wherein the step of generating the image signal includes:
 illuminating the target and an area near the target with a first image beam; and
 detecting a first image of the at least one marker formed by the first image beam.

16. The method as claimed in claim 15, wherein the step of generating the image signal further includes:
 illuminating the target and the area near the target with a second image beam unparallel to the first image beam; and
 detecting a second image of the at least one marker formed by the second image beam.

17. The method as claimed in claim 14, wherein the step of adjusting the radiation beam includes:
 superimposing the tracking signal on a radiation treatment plan; and
 generating a beam adjustment signal using the treatment plan with the tracking signal superimposed thereon.

18. The method as claimed in claim 14, wherein the first multi-leaf collimator has a plurality of movable leaves arranged in two rows opposite each other.

19. An apparatus for irradiating a target, comprising:
 a platform for supporting an object having a marker indicating a position of the target;
 a radiation source, said radiation source generating a radiation beam toward said platform;
 a beam adjuster between said radiation source and said platform, said beam adjuster comprising a first multiple leaf collimator;
 a first image detector, said first image detector generating a first image signal of the marker; and
 a control module coupled to said image detector to said beam adjuster, said control module generating a beam adjustment signal for controlling said first multiple leaf collimator to track a movement of the target in response to the first image signal;
 wherein said control module is configured to control said first multiple leaf collimator to perform an intensity modulated radiotherapy, and wherein in the intensity modulated radiotherapy, a leaf of the first multiple leaf collimator is adjusted such that a first portion of the target receives more radiation than a second portion of the target.

20. The apparatus of claim 19, said control module being further coupled to said platform and generating a control signal to move said platform in response to the first image signal.

21. The apparatus of claim 19, said first image detector including at least one device selected from a group of devices consisting of a video camera, an X-ray imager, a magnetic field detector, an ultrasound sensor, a computed tomography imager, a single photon emission computed tomography imager, a magnetic resonance imager, a magnetic resonance spectroscopy imager, and a positron emission tomography imager.

22. The apparatus of claim 19, further comprising a gantry, said gantry housing said radiation source and said beam adjuster.

23. The apparatus of claim 22, said control module being further coupled to said gantry and generating a control signal to move said gantry in response to the first image signal.

24. The apparatus of claim 19, further comprising a first image beam source generating a first image beam toward said platform, said first image detector generating the first image signal by detecting the first image beam.

25. The apparatus of claim 24, further comprising:
 a second image beam source, said second image beam source generating a second image beam toward said platform and unparallel to the first image beam; and
 a second image detector coupled to said control module, said second image detector generating a second image signal by detecting the second image beam.

26. The apparatus of claim 19, wherein said first multiple leaf collimator comprised of a first row of movable leaves and a second row of movable leaves opposite to each other.

27. The apparatus of claim 26, said beam adjuster further including a second multiple leaf collimator between said first multiple leaf collimator and said platform and comprised of a plurality of movable leaves unparallel to said first row and said second row of movable leaves in said first multiple leaf collimator.

28. A method for irradiating a target, comprising the steps of:
 using an internal anatomy of a patient as a marker;
 establishing a relationship of the marker relative to the target;
 generating an image signal of the marker;
 generating a tracking signal in response to the image signal; and
 adjusting a radiation beam in response to the tracking signal to track the target;
 wherein the target is tracked while performing an intensity modulated radiotherapy using a first multi-leaf collimator, and wherein in the intensity modulated radiotherapy, a leaf of the first multi-leaf collimator is adjusted such that a first portion of the target receives more radiation than a second portion of the target.

29. The method of claim 28, wherein the image signal is generated using a camera.

30. A process for irradiating a target in an animal body, comprising the steps of:
 collecting a plurality of images at a plurality of phases in a same physiological cycle, said plurality of images providing an indication of a location of the target relative to an internal marker;
 creating a treatment plan based at least in part on the plurality of images collected at the plurality of phases in the cycle; and delivering a radiation beam to the animal body according to said treatment plan;

wherein the radiation beam is delivered to perform an intensity modulated radiation therapy on a target of the animal body in which a first region of the target receives more radiation than a second region of the target while the target is being tracked, the target being tracked and the radiation beam being delivered by adjusting one or more leaves of a multi-leaf collimator.

31. The process of claim 30, wherein said internal marker comprises an anatomical structure.

32. The process of claim 30, wherein said internal marker is implanted in the animal body.

33. A method for irradiating a target, comprising:
determining a position of the target;
tracking the target based on the determined position; and
delivering radiation to perform an intensity modulated radiation therapy on the target while the target is being tracked;
wherein the target is tracked by adjusting one or more leaves of a multi-leaf collimator, and wherein the radiation is delivered by further adjusting one of the one or more leaves of the multi-leaf collimator to modulate an intensity of the radiation delivered to the target such that a first region of the target receives more radiation that a second region of the target.

34. The method of claim 33, wherein the target is tracked using an anatomical structure of a patient.

35. The method of claim 33, wherein the target is tracked using a marker externally placed on a patient.

36. The method of claim 33, wherein the target is tracked using a marker implanted within a patient.

37. The method of claim 33, wherein the position is determined using a camera.

* * * * *

UNITED STATES PATENT AND TRADEMARK OFFICE
CERTIFICATE OF CORRECTION

PATENT NO. : 7,221,733 B1  Page 1 of 1
APPLICATION NO. : 10/037477
DATED : May 22, 2007
INVENTOR(S) : Yoshihiro Takai et al.

It is certified that error appears in the above-identified patent and that said Letters Patent is hereby corrected as shown below:

In column 7, line 53, delete ~~OR~~ and replace with <u>OF</u>.

IN THE CLAIMS:
Column 12, Claim 4 should read:
--The method as claimed in claim 1, wherein the step of generating an image signal further includes the steps of:
 illuminating the target and an area near the target with a first image beam; and
 detecting a first image of the at least one marker <u>formed</u> by the first image beam.--

Column 12, Claim 6 should read:
--The method as claimed in claim 1, wherein the step of adjusting a radiation beam further includes the steps of:
 <u>superimposing</u> the tracking signal on a radiation treatment plan; and
 generating a beam adjustment signal using the treatment plan with the tracking signal superimposed thereon.--

Signed and Sealed this

Fifteenth Day of April, 2008

JON W. DUDAS
*Director of the United States Patent and Trademark Office*